United States Patent [19]

Hasson et al.

[11] Patent Number: 5,743,884
[45] Date of Patent: Apr. 28, 1998

[54] SEALING STRUCTURE FOR MEDICAL INSTRUMENT

[76] Inventors: Harrith M. Hasson, 2043 N. Sedgewick, Chicago, Ill. 60614; Nick Lakatos, 1625 Elm St., Des Plaines, Ill. 60018

[21] Appl. No.: 493,492
[22] Filed: Jun. 22, 1995

Related U.S. Application Data

[63] Continuation-in-part of Ser. No. 992,495, Dec. 17, 1992, abandoned.

[51] Int. Cl.⁶ ............................................. A61M 5/178
[52] U.S. Cl. .................... 604/169; 604/167; 604/264; 604/249; 137/247.17
[58] Field of Search ........................... 604/173, 158, 604/164, 167, 169, 246, 249, 264, 247; 137/247, 247.11, 247.13, 247.17

[56] References Cited

U.S. PATENT DOCUMENTS

| | | | |
|---|---|---|---|
| 4,244,379 | 1/1981 | Smith | 604/247 |
| 4,387,879 | 6/1983 | Tauschinski | 604/247 |
| 4,895,346 | 1/1990 | Steigerwald | 604/247 |
| 5,002,557 | 3/1991 | Hasson . | |
| 5,009,391 | 4/1991 | Steigerwald | 604/247 |
| 5,071,411 | 12/1991 | Hillstead . | |
| 5,084,023 | 1/1992 | Lemieux . | |
| 5,125,910 | 6/1992 | Freitas . | |
| 5,158,553 | 10/1992 | Berry et al. . | |
| 5,180,376 | 1/1993 | Fischell . | |
| 5,205,834 | 4/1993 | Moorehead et al. | 604/247 |
| 5,219,329 | 6/1993 | Fischell et al. . | |
| 5,242,393 | 9/1993 | Brimhall et al. . | |
| 5,334,159 | 8/1994 | Turkel | 604/247 |
| 5,514,109 | 5/1996 | Mollenauer et al. | 604/247 |

Primary Examiner—Mark Bockelman
Assistant Examiner—Chalin Smith
Attorney, Agent, or Firm—Wood, Phillips, VanSanten, Clark & Mortimer

[57] ABSTRACT

A sealing structure for an elongate medical instrument. The sealing structure includes a first sealing member having a first body with oppositely facing first and second surfaces and a peripheral edge and a second sealing member having a second body with oppositely facing third and fourth surfaces and a peripheral edge. A housing has a peripheral wall to surroundingly engage the peripheral edges of the first and second bodies with the first and second sealing members in operative relationship, wherein the second surface on the first body facially abuts to the third surface on the second body. The first body has at least a first portion that is compressible and deformable, with the second body having at least a second portion that is likewise compressible and deformable. There is an opening in the first portion of the first body that extends through the first body from the first surface to the second surface. There is an opening in the second portion of the second body that extends through the second body from the third surface to the fourth surface. The openings in the first and second bodies are expandable to allow the first and second bodies to grippingly engage an elongate medical instrument extended through the openings in the first and second bodies with the first and second sealing members in operative relationship.

27 Claims, 11 Drawing Sheets

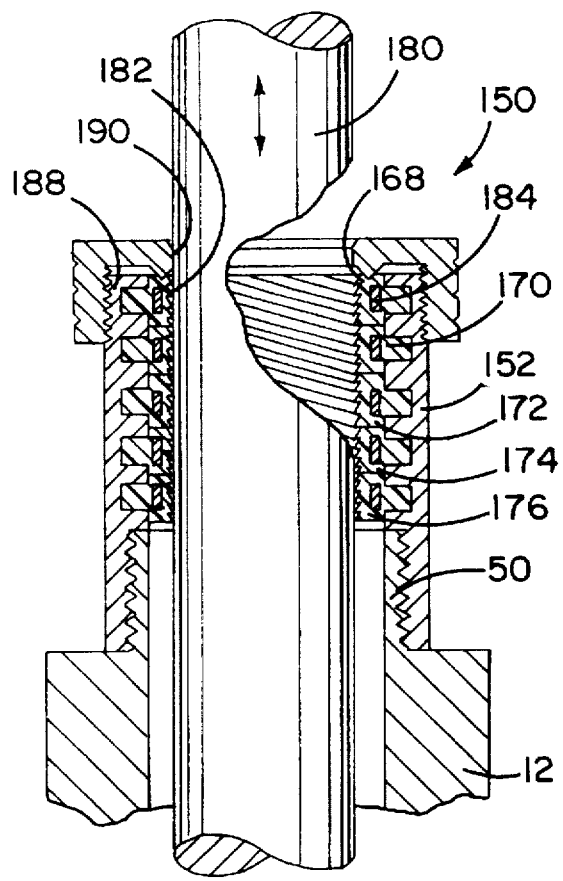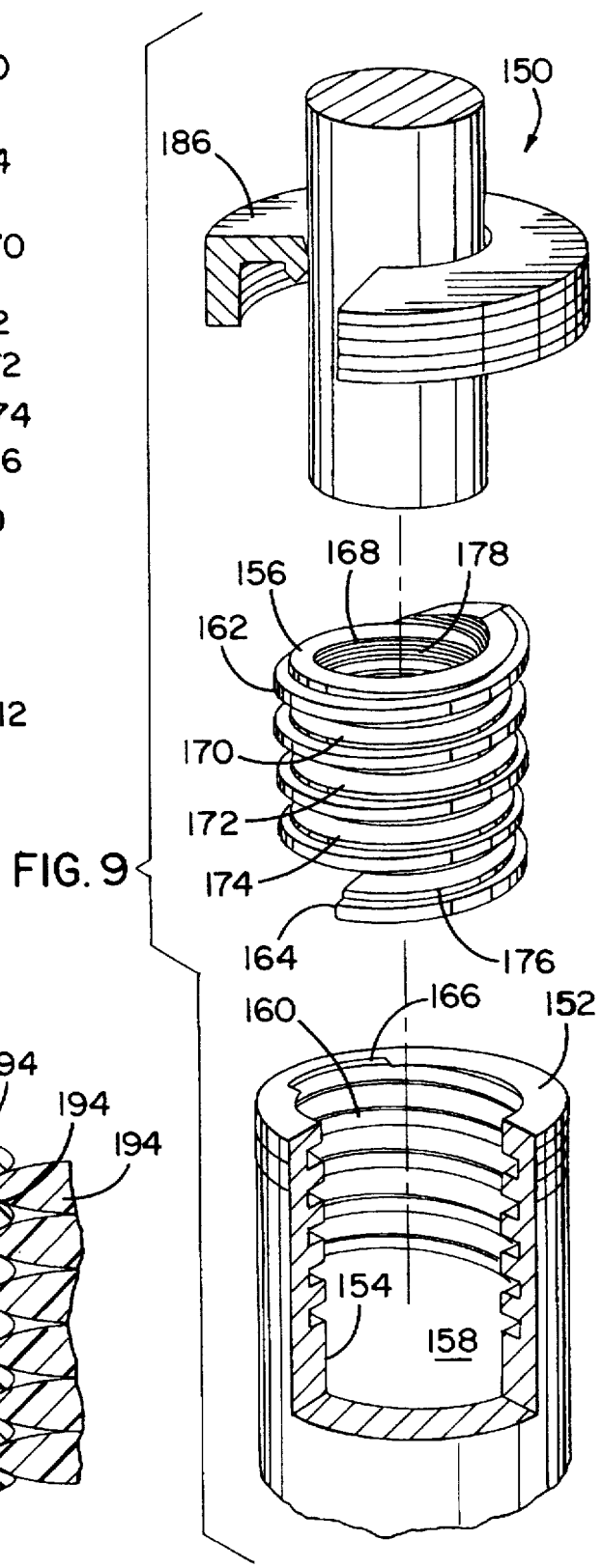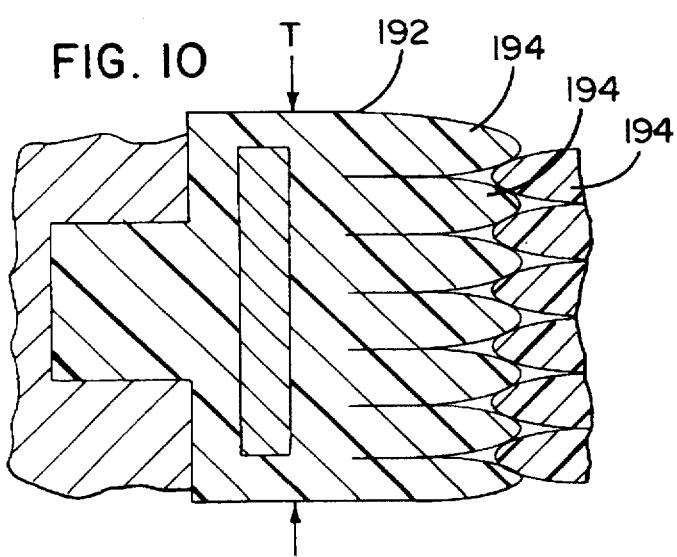

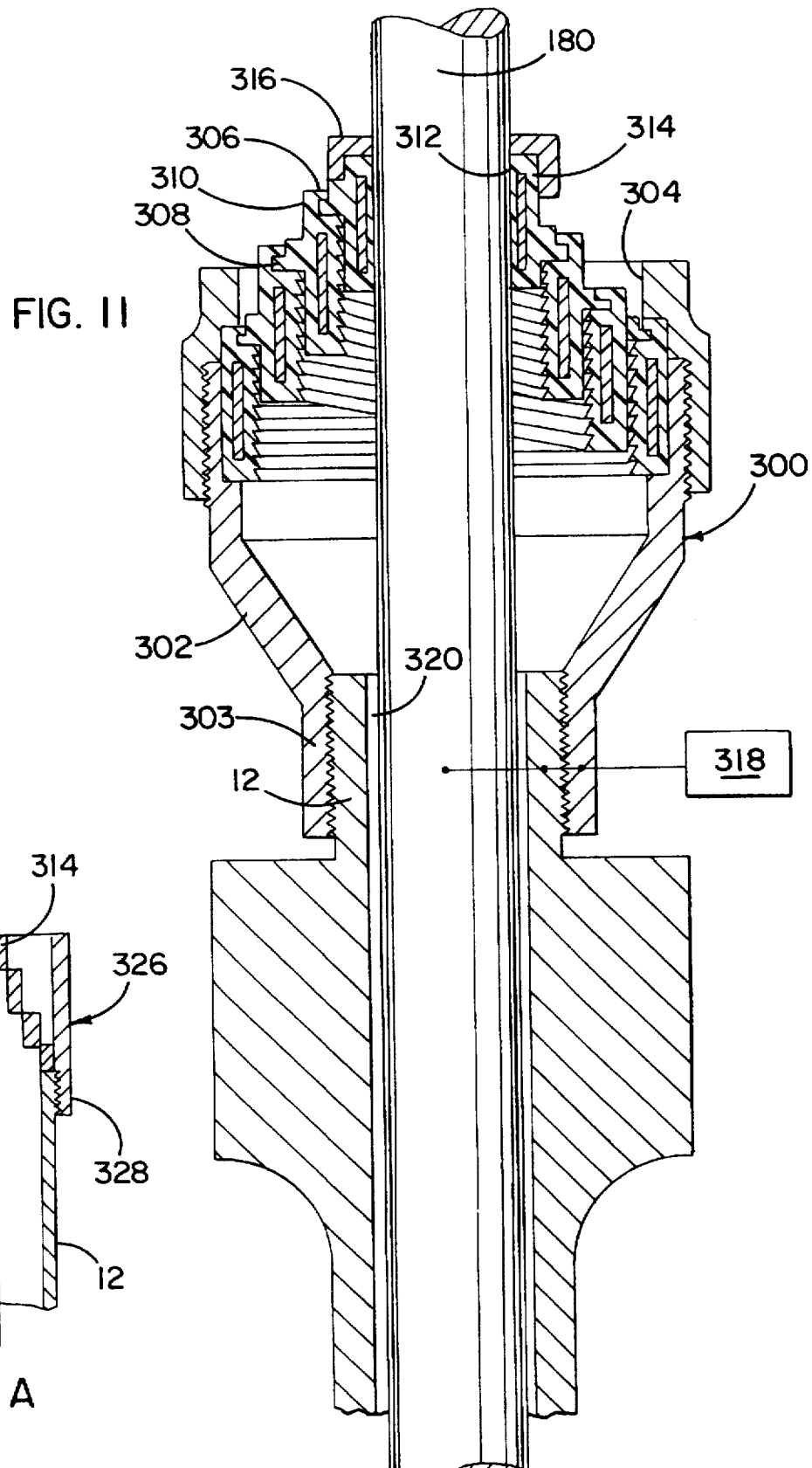

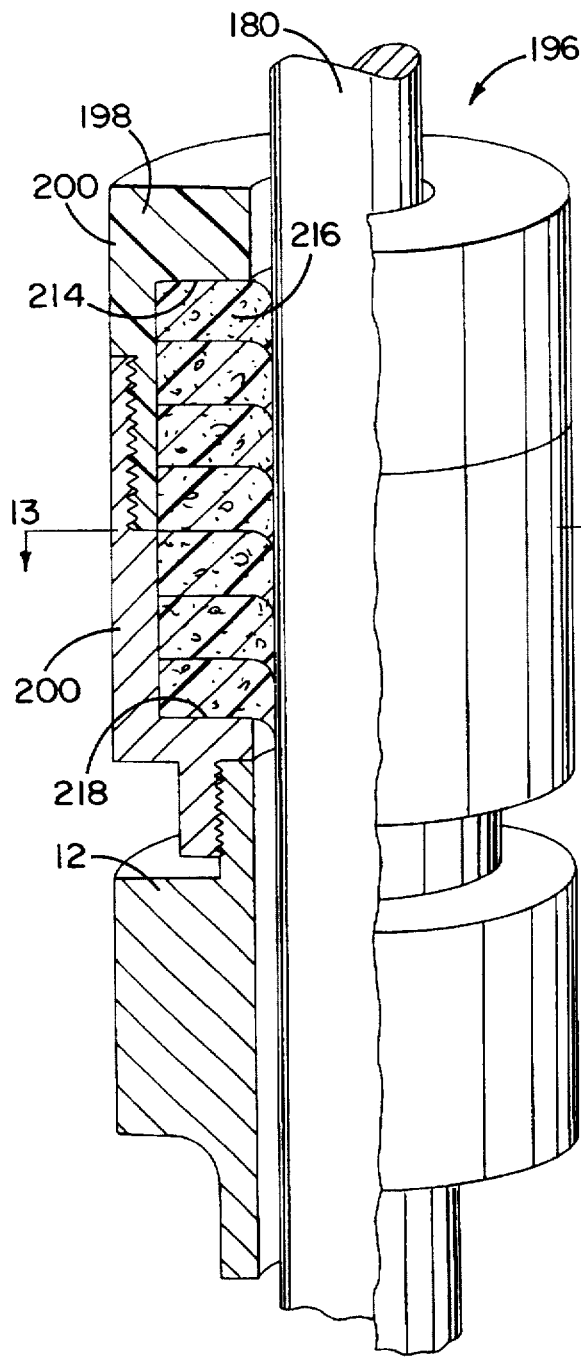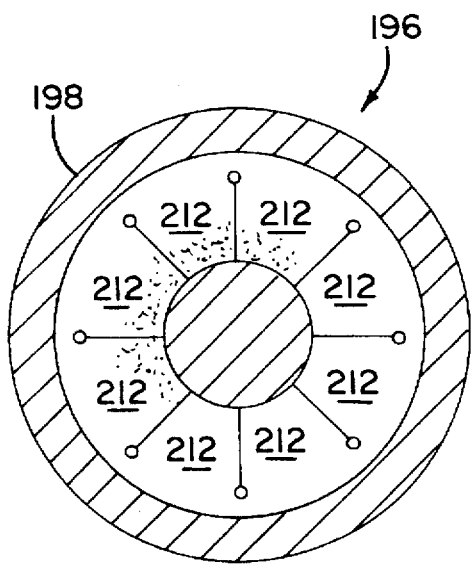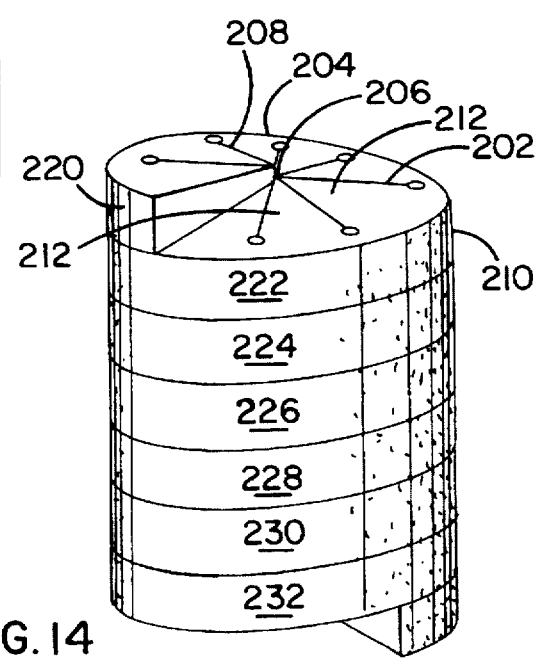
FIG. 12
FIG. 13
FIG. 14

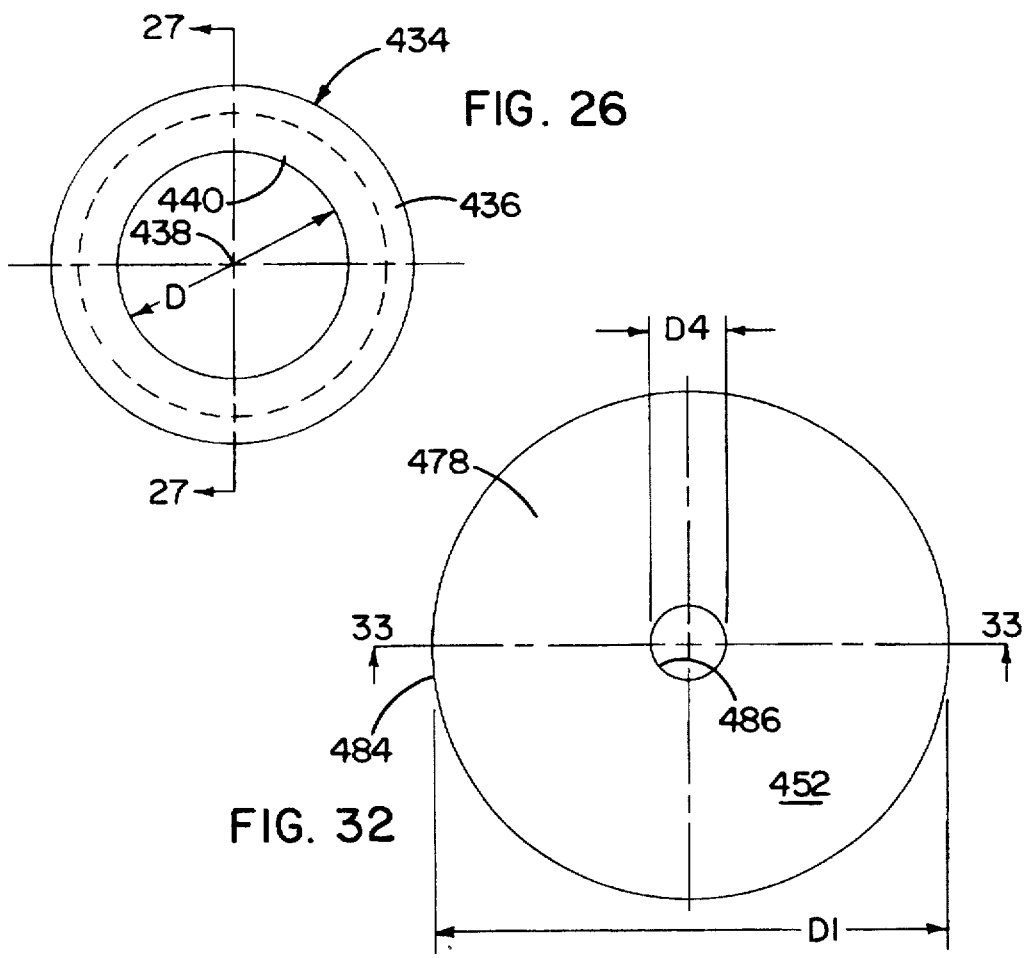
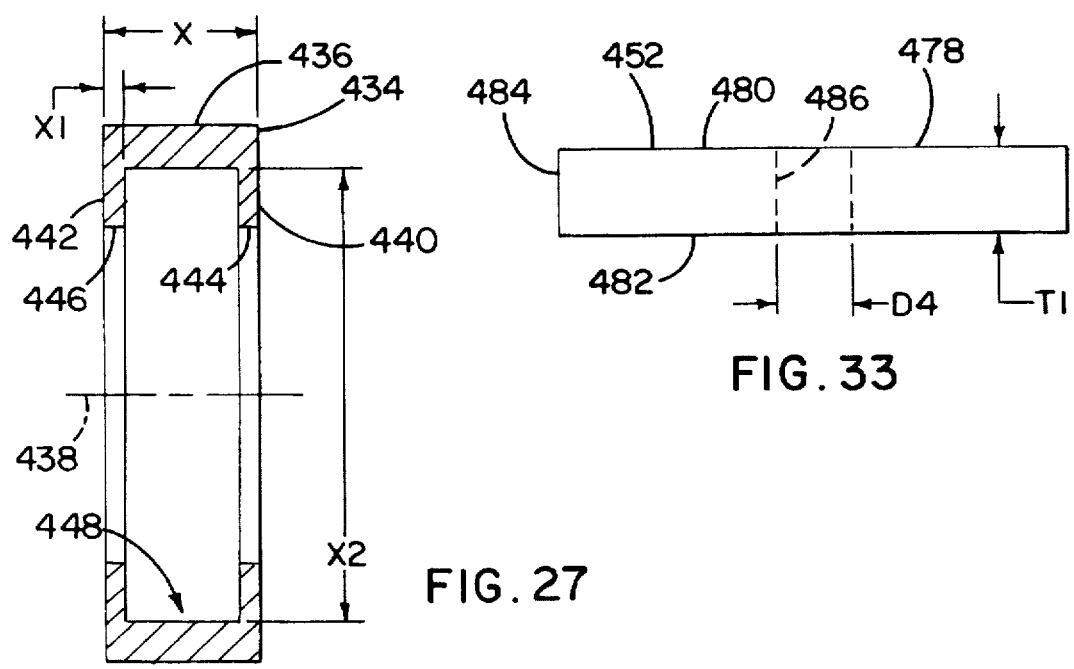
FIG. 26
FIG. 32
FIG. 33
FIG. 27

5,743,884

SEALING STRUCTURE FOR MEDICAL INSTRUMENT

CROSS-REFERENCE

This is a continuation-in-part of my U.S. application Ser. No. 07/992,495, entitled "Sealing Structure for Laparoscopic Cannula", filed Dec. 17, 1992, now abandoned.

BACKGROUND OF THE INVENTION

1. Field of the Invention

This invention relates to medical instruments and, more particularly, to a sealing structure that is penetrable by a medical instrument and which seals the entry to a passageway into which a medial instrument is directed.

2. Background Art

Laparoscopic surgery is, of late, widely used as a substitute for conventional surgery. In laparoscopy, a small incision is made in tissue to allow direction therethrough of a cannula which defines a passageway through the tissue for admittance of a wide range of surgical instruments. A gas is introduced through the cannula to distend the tissue and thereby enlarge the cavity in the vicinity of where a procedure is to be performed. A number of cannulas may be required to allow simultaneous introduction and manipulation of different surgical instruments.

One problem that has been contended with in the past is that of maintaining the gas within the cavity while allowing instruments to be directed into and withdrawn from the cavity. One proposed solution to this problem has been the provision of a sealing door that is pivotable between a) a closed position, wherein it seats against a wall so as to fully block the cannula passageway and b) an open position wherein the passageway is substantially unobstructed. The door is normally biased to its closed position. The door has a surface that is obliquely arranged with respect to the length of the cannula so that an instrument directed into the cannula towards the cavity progressively cams the door from its closed position into its open position.

This door arrangement has three principal drawbacks. First, it is a relatively complicated structure, requiting a hinge and spring structure to be fit in a very compact space. Second, the door performs virtually no sealing function in its open state, therefore requiring an effective redundant seal to prevent the escape of gas through the cannula passageway with the door in its open state. Third, the door creates interference with any foreign matter that may be removed from the cavity during laparoscopy. For example, it is common to morsel a growth within a cavity and to withdraw the mass piecewise through the cannula passageway. The morselled mass tends to snag on the free door edge, which is normally biased towards an interfering position within the passageway. This snagging may preclude withdrawal of the mass altogether or might alternatively cause a severance of a portion of the mass which then becomes undesirably lodged within the cannula in the vicinity of the door.

Another conventional sealing structure is made in the form of a membrane which spans the opening of the passageway. The membrane may be part of a cap that is friction fit to the end of the cannula. A plurality of radial slits are provided emanating from the center of the membrane to define triangularly shaped flaps which simultaneously deform as an instrument is forced therethrough.

There are several drawbacks associated with the above membrane. First of all, the membrane is often provided with a small central opening to prevent interference between the tips of the flaps and allow proper mashing of the flap edges to afford the most positive seal. With the instrument removed, the central opening defines an escape route for gas from within the cavity.

Another problem is that the membrane slits are usually defined so as to optimally seal a certain diameter of instrument. Instruments having diameters different than that for which the membrane is designed may compromise the seal.

Still further, in designing such a membrane, one balances the competing objectives of providing a membrane that is flexible enough to readily deform to allow admittance and withdrawal of the instruments, yet one which has sufficient memory to quickly and positively assume its undeformed, sealing state.

For want of a better solution, those in the medical profession have heretofore lived with the above problems in spite of the serious ramifications from a failed sealed. Escape of the gas during a procedure might be sufficient to require an interruption of the procedure and reintroduction of additional gas. A rapid escape of the gas could result in a collapse of the tissue around the area within which the surgical procedure is performed. This may result in a loss of the required visibility in the cavity, and in a worse case, injury to the patient.

SUMMARY OF THE INVENTION

In one form of the invention, a sealing structure is provided for an elongate medical instrument. The sealing structure includes a first sealing member having a first body with oppositely facing first and second surfaces and a peripheral edge and a second sealing member having a second body with oppositely facing third and fourth surfaces and a peripheral edge. A housing has a peripheral wall to surroundingly engage the peripheral edges of the first and second bodies with the first and second sealing members in operative relationship, wherein the second surface on the first body facially abuts to the third surface on the second body. The first body has at least a first portion that is compressible and deformable, with the second body having at least a second portion that is likewise compressible and deformable. There is an opening in the first portion of the first body that extends through the first body from the first surface to the second surface. There is an opening in the second portion of the second body that extends through the second body from the third surface to the fourth surface. The openings in the first and second bodies are expandable to allow the first and second bodies to grippingly engage an elongate medical instrument extended through the openings in the first and second bodies with the first and second sealing members in operative relationship.

In one form, the housing wall is rigid so that an elongate medical instrument extended through the openings in the first and second bodies in their operative relationship compresses the first and second portions of the bodies against the peripheral wall of the housing.

In one form, the housing has a center axis around which the peripheral wall extends and the housing has a first rim projecting radially inwardly from the peripheral wall and a second rim spaced axially from the first rim and projecting radially inwardly from the peripheral wall. The first and second sealing members reside between the first and second rims with the first and second sealing members in operative relationship and in assembled relationship with the housing.

In one form, the peripheral edge of the first body has a first effective diameter, the first rim has a radially inwardly facing edge defining a second effective diameter, and the first effective diameter is greater than the second effective diameter so that the first body must be radially compressed to be placed between the first and second rims on the housing.

The peripheral edge of the second body may have a third effective diameter, with the second rim having a radially inwardly facing edge defining a fourth effective diameter, with the third effective diameter being greater than the fourth effective diameter so that the second body must be radially compressed to be placed between the first and second rims on the housing.

The first body has a thickness between the first and second surfaces that is preferably no more than ¼ inch and, in one form, on the order of 1/16 inch. The second body has a similar thickness that is no more than ¼ inch and, in one form, on the order of 1/16 inch.

The first and second portions on the first and second bodies may be made from silicone rubber.

A third sealing member can be provided with the third body having oppositely facing fifth and sixth surfaces anti a peripheral edge. With the first, second and third sealing members in operative relationship, the fifth surface on the third body facially engages the fourth surface on the second body. The third body has at least a third portion that is compressible and deformable, with there being an opening in the third portion of the third body that extends through the third body from the fifth surface to the sixth surface. The opening in the third body is expandable to allow the third body to grippingly engage an elongate medical instrument extended through the opening in the third body. The peripheral wall of the housing surroundingly engages the peripheral edge of the third body with the first, second and third sealing members in operative relationship. The openings in the first, second and third portions of the first, second and third bodies are aligned to allow an elongate medical instrument to be directed guidingly through the first, second and third openings to thereby be grippingly engaged by the first, second and third bodies.

In one form, the opening in the second portion of the second body is defined by a substantially cylindrical cut-out. The opening in at least one of the first and third portions of the first and third bodies may be defined by at least one slit. More preferably, there are crossing slits that define independently movable and deformable flaps. In one form, there are at least six deformable flaps in the at least one of the first and third portions of the first and third bodies.

The openings in the first and second portions of the first and second bodies may have the same or a different configuration.

The invention also contemplates the above sealing structure in combination with an elongate medical instrument having a substantially cylindrical body extending through the openings in the first and second portions of the first and second bodies.

In another form of the invention, a sealing structure is provided for an elongate medical instrument, which sealing structure has a first disc-shaped sealing member having a first body with oppositely facing first and second flat surfaces and a peripheral edge, a second disc-shaped sealing member having a second body with oppositely facing third and fourth flat surfaces and a peripheral edge, and a third disc-shaped sealing member having a third body with oppositely facing fifth and sixth flat surfaces and a peripheral edge. The first, second and third sealing members, in an operative relationship, engage each other with the second flat surface on the first body facially abutting the third flat surface on the second body and the fourth flat surface on the second body facially abutting the fifth flat surface on the third body. The first body has at least a first portion that is compressible and deformable, with there being an opening through the first portion extending from the first flat surface to the second flat surface. The second body has at least a second portion that is compresssible and deformable, with there being an opening through the second portion extending from the third flat surface to the fourth flat surface. The third body has at least a third portion that is compressible and deformable, with there being an opening through the third portion extending from the fifth flat surface to the sixth flat surface. The openings in the first, second and third portions of the first, second and third bodies are aligned with the first, second and third sealing members in operative relationship so that an elongate medical instrument can be directed through the openings in the first, second and third portions of the first, second and third bodies to be grippingly engaged by the first, second and third portions of the first, second and third bodies.

A housing may be provided having a peripheral wall extending around a central axis, with a first rim extending radially inwardly from the peripheral wall and a second rim extending radially inwardly from the peripheral wall and spaced axially from the first rim relative to the central axis of the homing. The first, second and third sealing members in the operative relationship reside between the first and second rims and are confined against movement axially relative to the housing by the first and second rims with the first, second and third sealing members in assembled relationship with the housing.

The opening in at least one of the first, second and third bodies is defined by at least one slit such that the opening in the at least one of the first, second and third body is sealed in the absence of an elongate medical instrument being extended therethrough.

The opening in another of the first, second and third bodies can be defined by a substantially cylindrical cutout in the another of the first, second and third bodies.

In one form, the opening in each of the first and third portions of the first and third bodies is defined by at least one slit, with the opening in the second portion of the second body being defined by a cutout.

BRIEF DESCRIPTION OF THE DRAWINGS

FIG. 8 is a cross-sectional view of another form of sealing mechanism, according to the present invention, operatively connected to a cannula sleeve with an instrument extended therethrough and including a sealing member in the form of a strip thereon;

FIG. 9 is an exploded perspective view of the sealing mechanism and cannula sleeve in FIG. 8;

FIG. 10 is an enlarged cross-sectional view of a modified form of sealing member, according to the present invention, for use as with a sealing mechanism as shown in FIG. 8 and 9;

FIG. 11 is a cross-sectional view of a modified form of sealing mechanism, according to the present invention, operatively connected to a cannula sleeve with an instrument extended therethrough and showing a spirally wound sealing member;

FIG. 11A is a schematic representation of a modified form of sealing mechanism, similar to that in FIG. 11, and operatively connected to a cannula sleeve with an instrument extended therethrough.

FIG. 12 is a perspective view of a modified form of seating mechanism, according to the present invention, operatively connected to a cannula sleeve with an instrument extended therethrough;

FIG. 13 is a cross-sectional view of the sealing mechanism taken along line 13—13 of FIG. 12;

FIG. 14 is an isolated perspective view of a sealing member on the sealing mechanism in FIGS. 12 and 13;

FIG. 26 is an enlarged, plan view of a housing on the inventive sealing structure of FIG. 25;

FIG. 27 is a cross-sectional view of the housing taken along line 27—27 of FIG. 26;

FIG. 30 is an enlarged, plan view of one form of sealing member in FIGS. 28 and 29;

FIG. 31 is a cross-sectional view of the sealing member taken along line 31—31 of FIG. 30;

FIG. 32 is an enlarged, plan view of a second form of sealing member in FIG. 29; and FIG. 33 is a cross-sectional view of the sealing member taken along line 33—33 of FIG. 32.

DETAILED DESCRIPTION OF THE DRAWINGS

Figure 1:
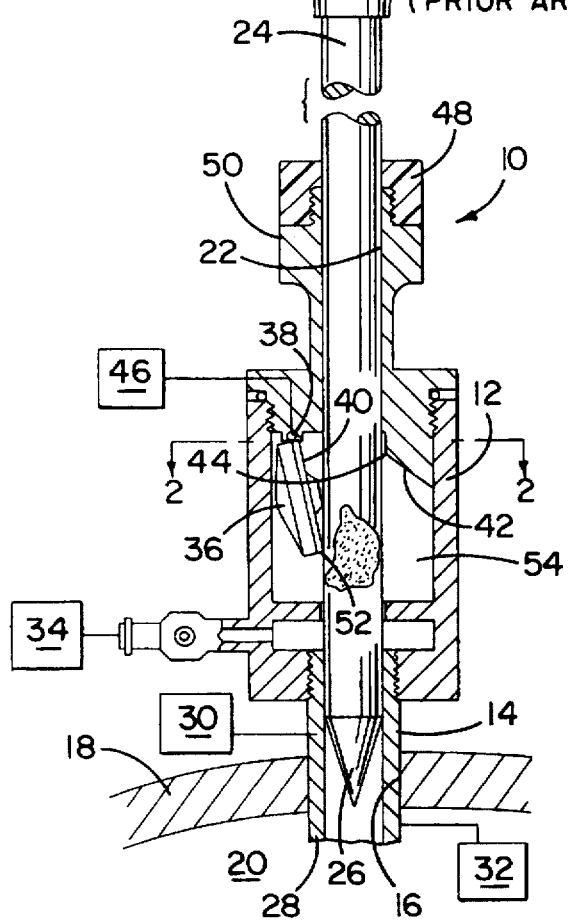
FIG. 1 is a cross-sectional view of a prior art cannula defining an internal passageway for an instrument and with a trocar extended through the passageway so that a sealing door thereon is placed in an open position.
Figure 2:
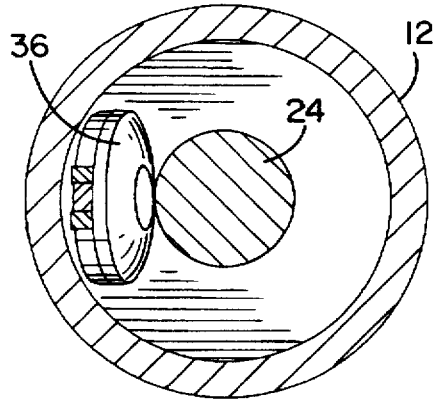
FIG. 2 is a cross-sectional view of the cannula taken along line 2—2 of FIG. 1.

In FIGS. 1 and 2, a prior art cannula is shown at 10, which cannula 10 includes an elongate sleeve 12 having a portion 14 thereof extending through an incision 16 in a tissue 18 bounding a cavity 20 in which a procedure is to be performed. The sleeve 12 defines an internal passageway 22 from a point externally of the cavity 20 through the tissue 18 and into the cavity 20. The passageway 22 accommodates any of a number of different types of surgical instruments (not shown).

To initiate a procedure using the cannula 10, a trocar 24, having a pointed free end 26, is directed through the passageway 22 until the free end 26 thereof is exposed beyond the free distal end 28 of the sleeve 12. The free end 26 of the trocar 24 guides movement of the sleeve 12 through the incision 16 sufficiently that the sleeve end 28 is exposed within the cavity 20. Sealing structure, shown schematically at 30, 32, on opposite sides of the tissue 18, is provided to both seal around the incision 16 with the cannula 10 in an operative position and stabilize the cannula 10 in the operative position shown in FIG. 6. The details of suitable sealing structure 30, 32 are disclosed fully in my U.S. Pat. No. 5,002,557.

Once the cannula 10 is in its operative position, gas from a supply 34 is directed into the cavity 20 to distend the tissue 18 and thereby enlarge the cavity 20 around the working site. This allows unobstructed movement of the surgical instruments and the required visibility to effectively manipulate the same.

To maintain the distending gas within the cavity 20, a pivotable door 36 is provided on the sleeve 12. The door 36 is connected to the sleeve 12 through a pin 38 which allows the door 36 to pivot between an open position, shown in FIG. 6, and a closed position, wherein a sealing surface 40 bears against an inclined wall 42 on the sleeve 12 to seal a port 44 on the sleeve wall 42. With the door 36 in its closed position, flow of gas from the cavity 20 back through the passageway 22 is prohibited.

With the door 36 in the closed position therefor, the sealing surface 40 is arranged obliquely with respect to the lengthwise axis of the sleeve 12. Introduction of the trocar 24 or surgical instrument (not shown) into the passageway 22 causes the free end 26 thereof to encounter the door surface 40 to progressively cam the door 36 from its closed position into its open position. The door 36 remains open so long as the trocar 24/instrument resides within the passageway 22. Upon removal of the trocar 24/instrument from the passageway 22, a spring 46 biases the door 36 back into its closed position.

The door 36 has several problems associated therewith. First of all, with the door 36 held in its open state by the trocar 24/instrument, the space around the port 44 remains unsealed. Accordingly, to prevent the unimpeded escape of gas from the cavity 20, a gasket element 48 is required to seal the proximal end 50 of the sleeve 12.

A further problem is that the door 36 interferes with any mass that may be removed with a surgical instrument from the cavity 20 through the passageway 22. The door 36 has an edge 52 that rides along the trocar 24/instrument as the trocar 24/instrument is extended into and withdrawn from the passageway 22. Upon withdrawing a mass from the cavity 20, the mass encounters the edge 52 and will either block further withdrawal of the instrument or become severed which results in a portion of the mass becoming lodged in a cavity 54 within the sleeve 12.

Figure 3:
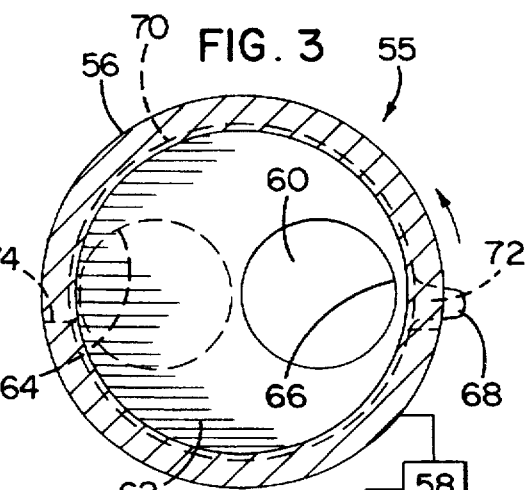
FIG. 3 is a plan view of a sealing mechanism, according to the present invention, and having first and second relatively rotatable members that can be placed selectively in open and closed states.
Figure 4:
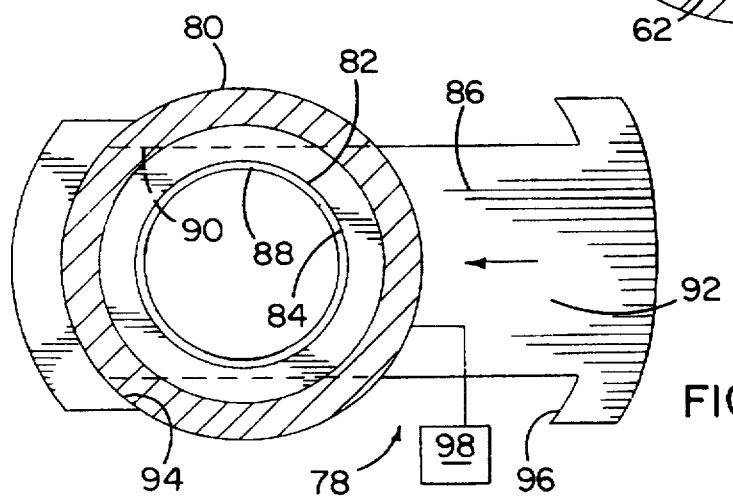
FIG. 4 is a plan view of a modified form of sealing mechanism, according to the present invention, having first and second members that are relatively repositioned by translation between open and closed states.
Figure 5:
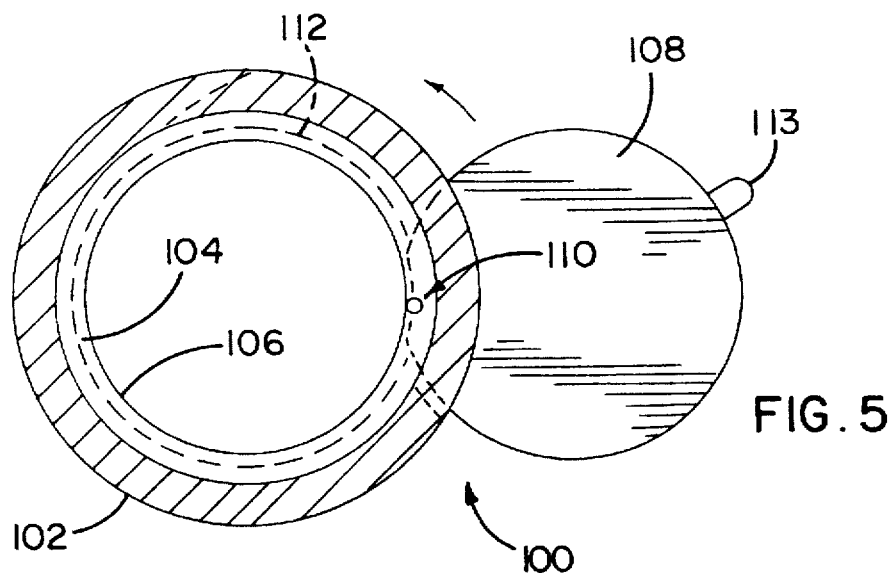
FIG. 5 is a plan view of another modified form of sealing mechanism, according to the present invention, and having a pivotable closure member.

The present invention is specifically directed to various structures for sealing the sleeve passageway 22 on a cannula 10 of the type shown in FIGS. 1 and 2 without the drawbacks of the prior art structures. In FIGS. 3–5, various sealing mechanisms/closures, according to the present invention, are disclosed.

In FIG. 3, a sealing mechanism is shown at 55, to include an end fitting 56, which has an axis alignable with the length of the sleeve 12, and is connectable to the proximal end 50 of the sleeve 12 through a means, shown schematically at 58. The means 58 may be a threaded connection, a friction fit, or the like.

The sealing mechanism 55 includes first and second disc-shaped sealing members 60, 62. The disc-shaped members 60, 62 are mounted in overlying relationship within the end fitting 56 for relative rotation. The first member 60 has a through opening 64 and the second member 62 a similarly shaped opening 66. In this case, at least the second member 62 is rotatable relative to the first member 60 between a first position, wherein the opening 66 is in registration with the opening 64, and a second position, wherein the openings 64, 66 are misaligned, as shown in FIG. 3, so that the members 60, 62 cooperatively block passage of a gas axially through the sealing mechanism 55.

Rotation of the member 62 can be effected through an external tab 68 projecting through a circumferential guide slot 70 in the end fitting 56. Shoulders 72, 74 block the tab 68 and thereby the plate 62 in each of the first and second positions, corresponding to the open and closed positions, respectively, for the sealing mechanism 55.

Another seating mechanism, according to the present invention, is shown at 78 in FIG. 4. The sealing mechanism 78 has an end fitting 80 with a first member 82 defining an axial through opening 84. A slide member 86 has a through opening 88 which is registrable with the opening 84 with the slide member 86 in a first, open position. The slide member 86 is translatable guidingly within a slot 90 defined by the end fitting 80 from the open position to a closed position, wherein a solid portion 92 of the slide member 86 radially overlaps the opening 84 to at least partially, and potentially fully, block the opening 84 to thereby prevent passage of gas axially through the sealing mechanism 78.

The slide member 86 has oppositely facing shoulders 94, 96 which abut the end fitting 80 with the members 82, 86 in each of the open and closed positions therefor. Optional biasing structure 98 can be provided to urge the slide member 86 to one of the open and closed positions therefor.

In FIG. 5, another form of sealing structure, according to the present invention, is shown at 100. The sealing structure 100 includes an end fitting 102 having a first member 104 defining an axial through opening 106. A disc-shaped closure member 108 is attached to the end fitting 102 by a pin 110 for pivoting movement between an open position, shown in FIG. 5, and a closed position, wherein the closure member 108 fully covers the opening 106. The end fitting 102 has a slot 112 therein to accept the member 108. A tab 113 facilitates repositioning of the closure member 108.

With the sealing mechanisms 55, 78, 100, the sleeve passageway 22 can be conveniently, quickly, and positively opened and closed by the user.

Figure 6:
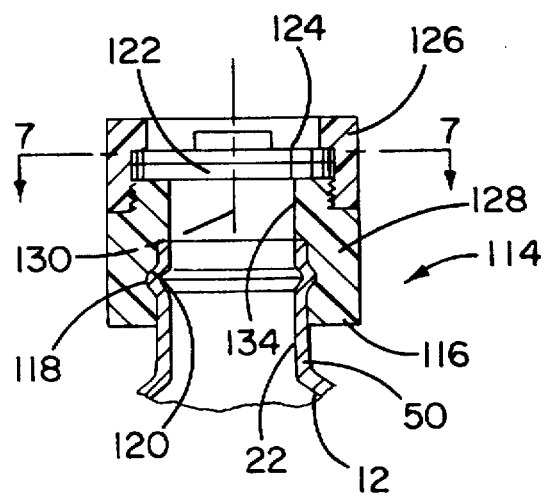
FIG. 6 is a fragmentary cross-sectional view of the end of a cannula sleeve having attached thereto one form of sealing mechanism, according to the present invention thereon.
Figure 7:
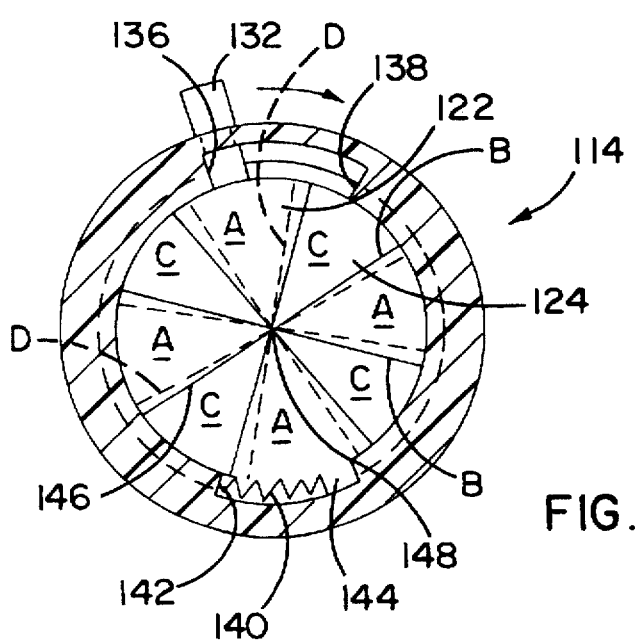
FIG. 7 is a cross-sectional view of the sealing mechanism taken along line 7—7 of FIG. 6.

In FIGS. 6 and 7, another form of sealing mechanism, according to the present invention, is shown at 114. The sealing mechanism has an end fitting 116 which, in this case, is shown frictionally engaged with the proximal end 50 of the sleeve 12. An annular rib 118 seats in an undercut 120 in the end fitting 116 to maintain the end fitting 116 operatively connected to the sleeve 12.

First and second sealing members 122, 124 are provided within the end fitting 116. Each sealing member 122, 124 is disc-shaped with the members 122, 124 placed in stacked, abutting relationship.

The end fitting 116 is defined by two threadably joined parts 126, 128 which captively maintain the sealing members 122, 124 in their operative relationship shown in FIGS. 6 and 7. The parts 126, 128 are separable to assemble, and allow replacement of, the members 122, 124. In their operative relationship, the members 122, 124 are rotatable relative to each other about the axis 130 of the end fitting 116 and sleeve 12.

The first and upper sealing member 122 has alternating, triangularly-shaped solid potions A and cutouts B. The sealing member 124 has alternating triangularly-shaped solid portions C and cutouts D.

In FIG. 7, the first and second members 122, 124 are shown in a closed position, wherein the solid portions A of the first member 122 overlie and fully cover the cutouts D in the second member 124. Rotation of the member 124 about the axis 130 through a tab 132 can be carded out to effect registration of the cutouts B in the member 122 and D in the member 124. This registration of cutouts B, D results in the definition of a continuous passageway 134 axially through the sealing members 122, 124 and end fitting 116 into communication with the sleeve passageway 22.

The solid portions A, C of the members 122, 124 can be made from a rubber or equally resilient material to allow deflection thereof downwardly by an instrument being pressed through the passageway 134.

The tab 132 is abuttable to oppositely facing shoulders 136, 138 defined by the end fitting 116 to thereby block the tab 132 in each of the first/open and second/closed positions for the members 122, 124. An optional coil spring 140 acts between a shoulder 142 on the end fitting and a tab 144 on the member 122, at a location diametrically opposite to the tab 132, to thereby urge the member 122 into the FIG. 7/closed position.

The center 146 of the solid portions A and cutouts B is shown to be slightly radially offset from the center 148 of the solid portions in C and cutouts D in the member 124 so that the centers 144, 146 are not aligned to define an escape route for gas from the sleeve passageway 22.

In FIGS. 8 and 9, a modified form of sealing mechanism, according to the present invention, is shown at 150. The sealing mechanism 150 has an end fitting 152 threadably connected to the end of the sleeve 12. As with all embodiments of end fitting herein, the threaded connection thereof permits different end fittings to be used on a single sleeve 12 for versatility. The end fittings can also be conveniently removed for cleaning.

The end fitting 152 has an axial through opening 154 within which a strip-like sealing member 156 is mounted. The inside wall 158 of the end fitting 152 bounding the opening 154 defines a spiral track 160 to accept the sealing member 156. The sealing member 156 has a continuous peripheral rib 162 that is guided within the track 160.

To assemble the strip, the leading end 164 thereof is introduced to the slot entryway 166, whereupon the sealing member 156 can be threaded into its operative position. This arrangement produces a plurality of axially spaced turns 168, 170, 172, 174, 176 which may be abutted to each other, as shown in FIG. 8, or axially spaced.

The radially inwardly facing surface 178 of the sealing member 156 is constructed to closely embrace an instrument 180 directed through the sealing mechanism 150. The surface 178 may have individual fingers 182 thereon or may be uninterrupted. The material making up the sealing member 156 may be rubber, foam, or other sponge-like or readily deformable material with good memory. In the case of a highly flexible material, a reinforcing element 184 may be required to maintain the shape of the sealing member 156 as it is threaded into its operative position. The sealing member 156 has a thickness preferably on the order of ⅛-¼ inch.

A supplemental sealing element, in the form of a cap 186, can be press fit to the open end 188 of the end fitting 152. The cap has a sealing surface 190 configured to closely grip the instrument 180. Alternatively, any of the sealing mechanisms shown in FIGS. 3-7 herein could be utilized in place of the cap 186.

FIG. 10 shows an alternative form of sealing member 192, also in the form of a strip. The ship has individual fingers 194 projecting radially into the through opening 154. The fingers 194 are sufficiently long that they mesh between adjacent fingers 194 projecting from a diametrically opposite location on the sealing member 192. The fingers 194 act much the same as bristles on a brush. In a meshed state, they perform a sealing function. By providing a plurality of axially spaced layers of fingers 194, the sealing function is enhanced. The sealing member 192 can be alternatively in the form of a disc wherein a single thickness T is defined for the sealing member 192.

The fingers 194 are preferably made from a resilient material with good memory. Rubber would be a suitable material. Alternatively, a sponge-like material could be utilized.

In addition to performing a sealing function, the fingers 194 wipe the instrument 180 as it is removed to effect cleaning thereof. However, the fingers 194 are sufficiently resilient to deform and thereby allow a mass from within the cavity to be passed therethrough without severance.

A further modified form of sealing mechanism, according to the present invention, is shown at 196 in FIGS. 12-14. The sealing mechanism 196 has an end fitting 198 defined by first and second threadably connected parts 200, 202. The end fitting 198 is in turn threaded to the sleeve 12 to be conveniently assembled thereto and readily removed therefrom.

In the mechanism 196, a sealing member 204 is defined by a coil of resilient material, such as foam or other sponge-like material. The sealing member 204 has a central, axial through opening 206 which is normally in a closed state. A plurality of radially extending slits 208 emanate from the center 206 and project to adjacent the peripheral outer surface 210 of the sealing member 204 so as to define individual flaps 212. The slits 208 are uniformly spaced so as to define in this case eight identical flaps 212.

The sealing member 204 is received within a chamber 214 defined between axially oppositely facing shoulders 216, 218 on the end fitting parts 200, 202, respectively. Upon the instrument 180 being directed through the sealing mechanism 196, the flaps 212 deform by compression radially outwardly to enlarge the through opening 206 to accommodate the instrument 180. The flaps 212 on the turns 220, 222, 224, 226, 228, 230, 232 deform in succession as the instrument 180 is inserted. Accordingly, accommodation of the instrument 180 is made primarily by the compression of the sealing member 204 rather than a downward deflection of the individual flaps 212.

Figure 22:
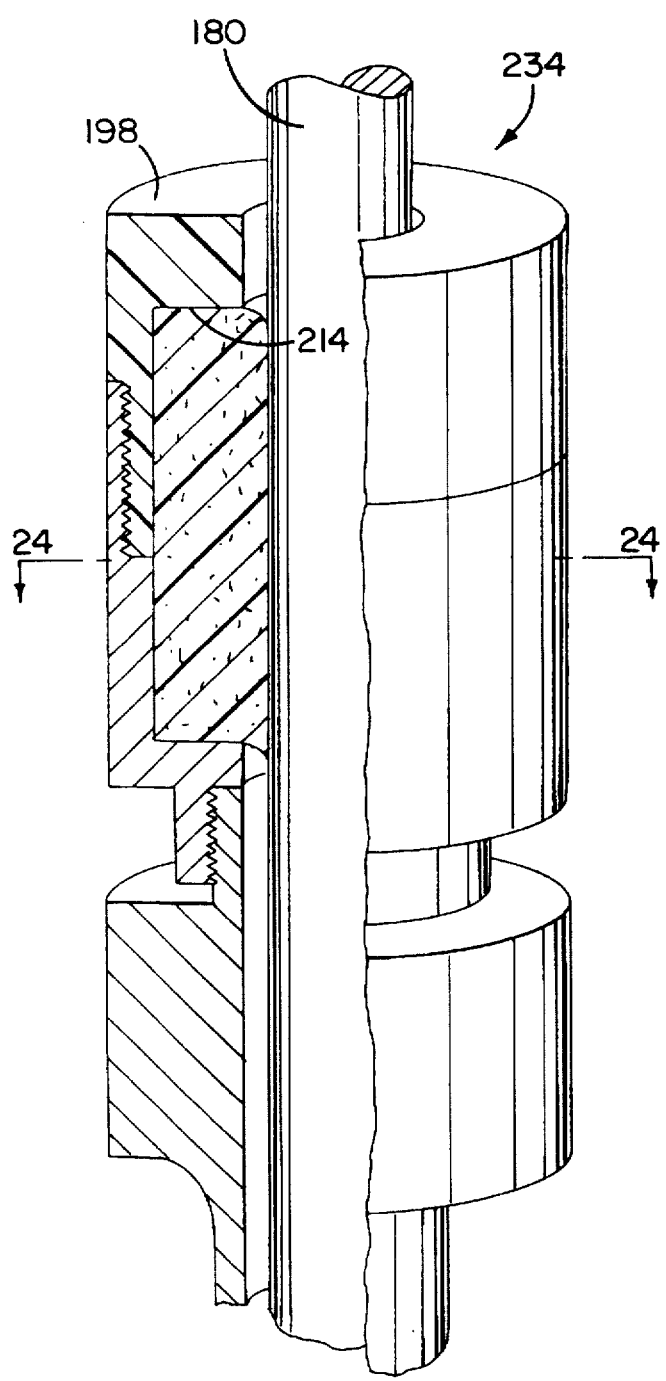
FIG. 22 is a perspective view of a sealing mechanism showing a further modified form of sealing member, according to the present invention, with an instrument extended therethrough.
Figure 23:
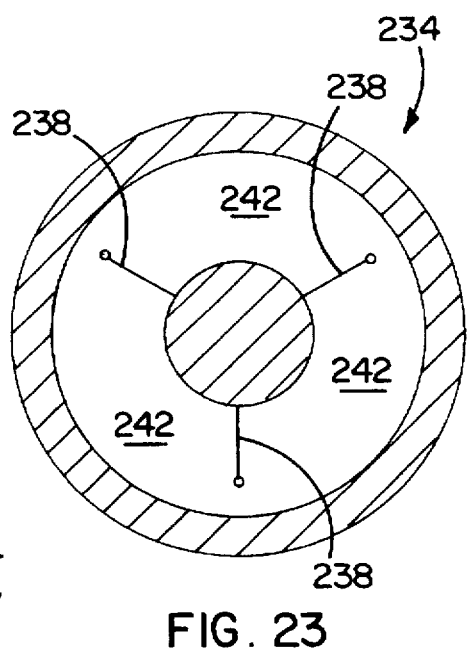
FIG. 23 is a cross-sectional view of the sealing mechanism taken along line 24—24 of FIG. 22.
Figure 24:
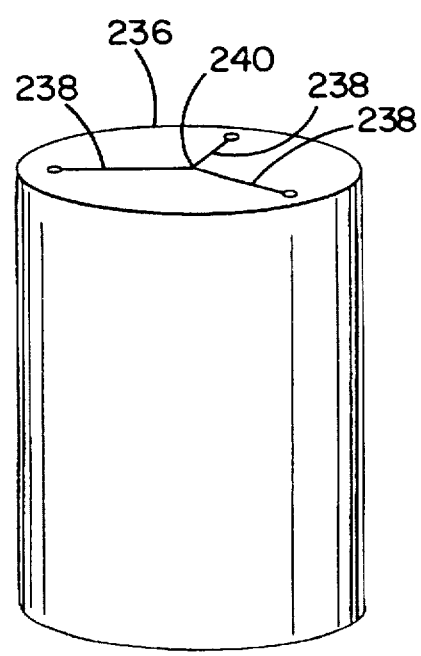
FIG. 24 is an isolated perspective view of the sealing member in FIGS. 22 and 23.

In FIGS. 22-24, a sealing mechanism is shown at 234 that is slightly modified from that 196 in FIGS. 12-14. The end fitting 198 is identical to that in FIGS. 12-14. The only difference in the structure is that a sealing member 236, which is held captive within the chamber 214, is made from a single block of compressible material, such as foam, or other sponge-like material. The axial thickness of the sealing member 236 may be from ½-1 inch or greater.

Three radial slits 238 extend from an axial through opening 240, that is normally substantially closed. Upon introduction of the instrument 180, the flaps 242 between adjacent slits 238 compress in a radial direction to enlarge the center opening.

Figure 15:
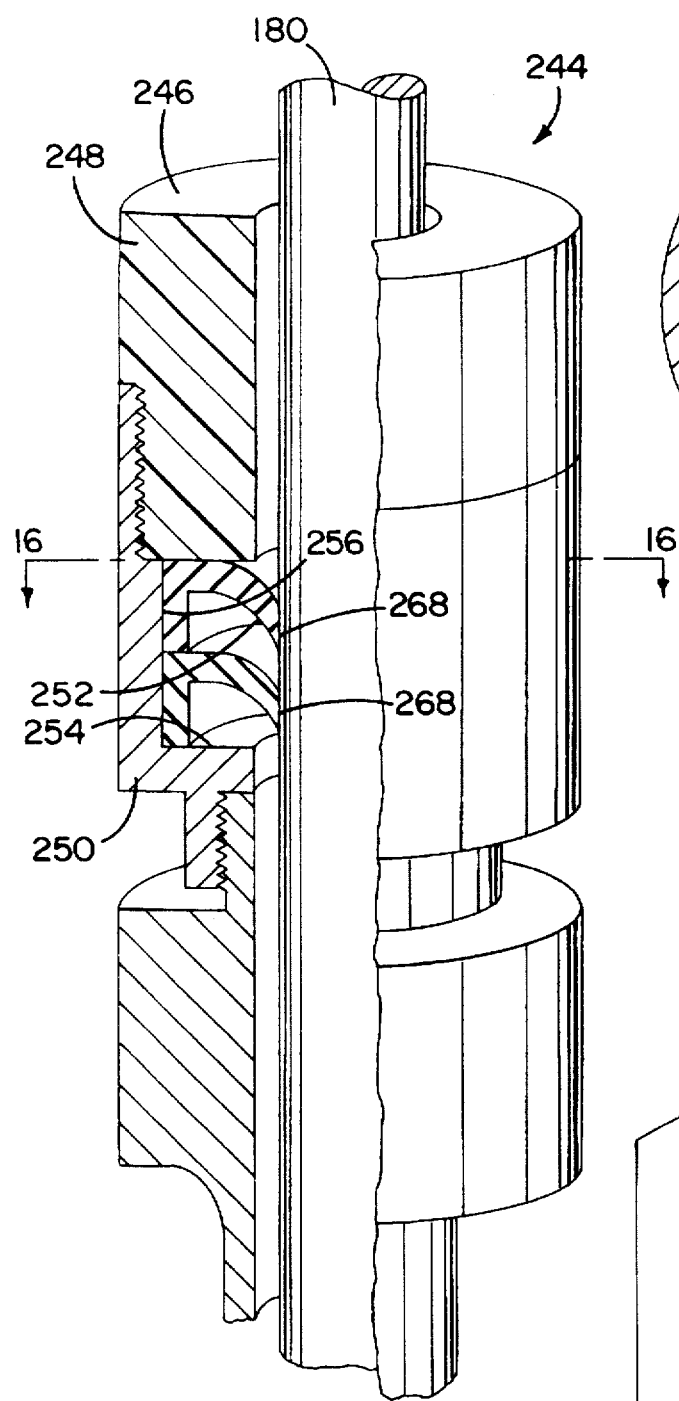
FIG. 15 is a perspective view of a sealing mechanism with a pair of sealing members, according to the present invention, operatively connected to a cannula sleeve with an instrument extended therethrough.
Figure 16:
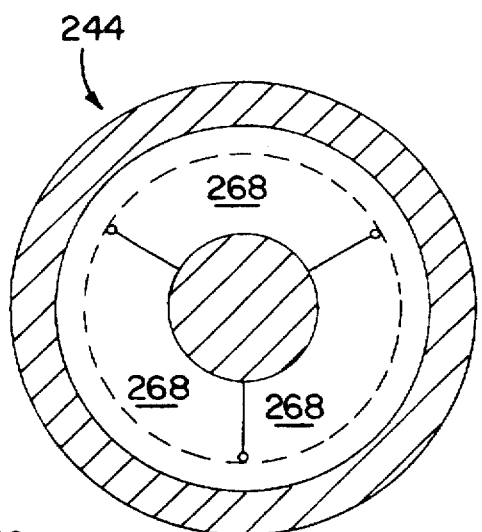
FIG. 16 is a cross-sectional view of the sealing mechanism taken along line 16—16 of FIG. 15.
Figure 17:
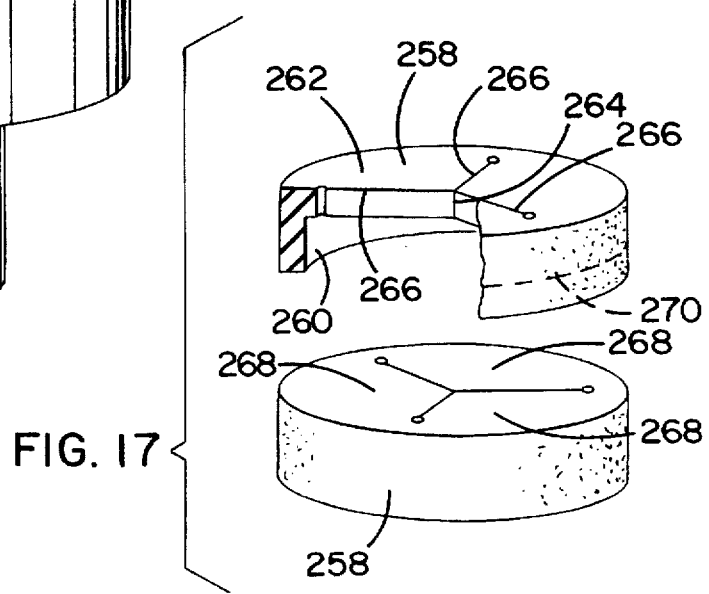
FIG. 17 is an isolated perspective view of the two sealing members in FIGS. 15 and 16.

In FIGS. 15-17, another form of sealing mechanism, according to the present invention, is shown at 244. The sealing mechanism 244 has an end fitting 246 defined by first and second threadably engaged parts 248, 250. The first and second parts 248, 250 have axially oppositely facing shoulders 252, 254 bounding a chamber 256 for reception of, in this case, two sealing members 258, each having the same construction. One, or more than two, sealing members 258 can be used.

Each sealing member 258 has a disc-shaped body 260 and a depending peripheral skirt 262 that serves principally as a spacer. The body 260 has a central axial through opening 264 that is normally closed. A plurality of radially extending slits 266, in this case three, define a like number of flaps 268 which are compressible outwardly as the instrument 180 is forced through the center opening 264.

The skirt 260 maintains the bodies 260 on the stacked sealing members 258 in spaced relationship to allow the flaps 268 to bend downwardly as well as compress in a radial direction, as seen clearly in FIG. 15. Depending upon the thickness of the bodies 260, the amount of deflection in an axial direction may be changed. For example, if the sealing members 258 are made from a sponge-like material that is at least of ¼ inch in thickness, the body 260 will have a tendency to maintain its shape so that enlargement of the central opening 264 is accomplished principally by compression of the flaps 268.

The skirts 260 could be eliminated so that only the body 260 remains, as shown in dotted lines 270 in FIG. 17. In this case, the sealing members 258 are stacked one against the other in an axial direction. In this arrangement, the slits 266 are preferably misaligned so that the underlying flaps 268 reinforce the overlying flaps 268 to prevent axial deflection thereof so that the enlargement of the opening 264 is principally accomplished by compression of the flaps 268 in a radial direction. At the same time, the misalignment of the slits 266 results in the underlying flaps 268 sealing the slits 266 immediately thereover.

Figure 20:
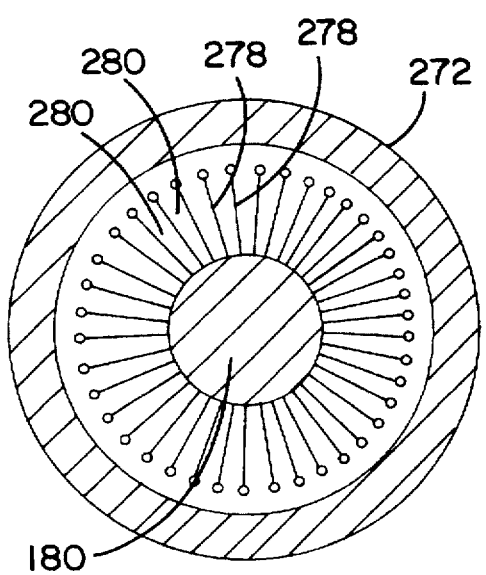
FIG. 20 is a plan view of a further modified form of sealing member, according to the present invention, with an instrument extended therethrough.
Figure 21:
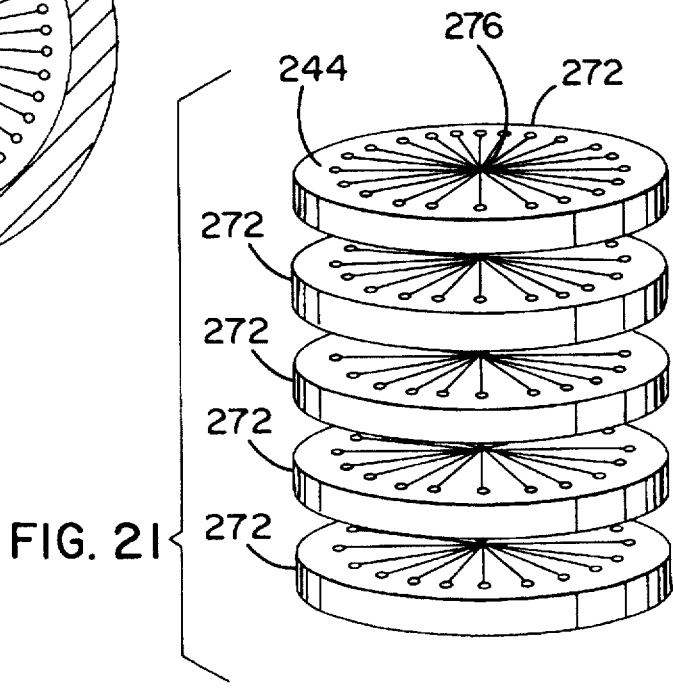
FIG. 21 is an exploded perspective view of a plurality of the sealing members in FIG. 20 shown in stacked relationship.

In FIGS. 20 and 21, another form of sealing member 272 is disclosed. The sealing member 272 has a body 274 with an axial through opening 276. Numerous radial slits emanate from the center opening 276 to define thin, readily deflectable flaps, which act much like the fingers 194 on the sealing member 192 in FIG. 10. The sealing member 272 is preferably made from a foam or other sponge-like material with good memory.

By stacking a plurality of the sealing members 272 upon each other in an end fitting (not shown), the underlying sealing members 272 reinforce the flaps 280 against axial deflection upon an instrument 180 being directed through the opening 276. Thus, the instrument 180 is accommodated principally by the radial deformation of the flaps 280. It is preferred that at least six and preferably a substantially larger number of flaps 280 be defined. It is also preferred that the slits 278 in any two vertically adjacent sealing members 272 be misaligned so that each slit 278 is normally sealed by an underlying flap 280.

Figure 18:
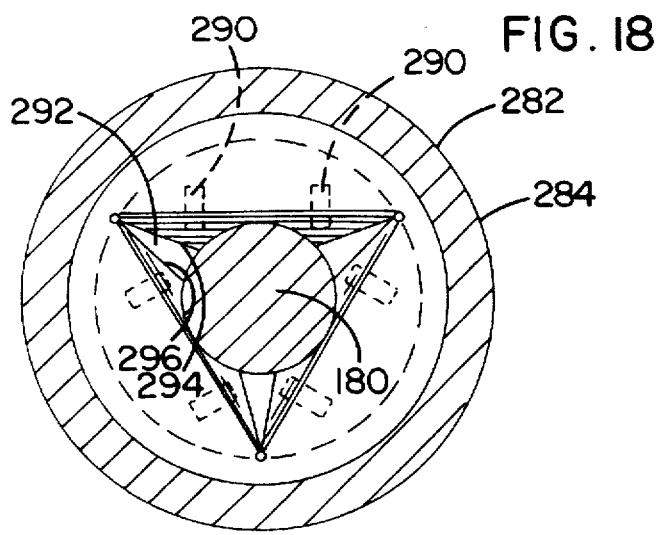
FIG. 18 is a plan view of a further modified form of sealing mechanism, according to the present invention, with an instrument extended therethrough.
Figure 19:
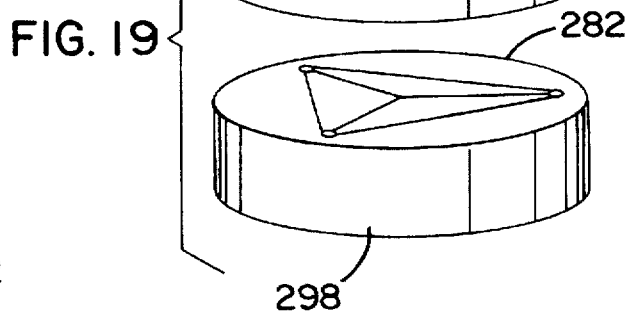
FIG. 19 is an exploded, isolated, perspective view of a pair of sealing members, as in FIG. 18, in stacked relationship.

In FIGS. 18 and 19, a further modified form of sealing member, according to the present invention, is shown at 282. The sealing member 282 has a body 284 defining an axial through opening 286. A plurality of flaps 288 are connected to the body by hinges 290 which permit the flaps 288 to be moved from the closed position in FIG. 19, to the open position in FIG. 18, wherein they are deflected by the instrument 180 directed through the opening 286. The hinges 290 include mean, such as springs, for normally biasing the flaps 288 to the closed position therefor.

To avoid the escape of gas from between adjacent flaps in the open position for the sealing member 282, a flexible membrane 292 can connect between the edges 294, 296 of two adjacent flaps 288. The membrane 292 is in a slackened state with the sealing member in a closed position and stretches with the flaps 288 in the open position of FIG. 18. The membrane 292 tends to hug the instrument 180 extended through the sealing member 282 to prevent the escape of gas through the opening 286. A single membrane 292 can be provided to extend completely around the through opening 286 and to closely embrace the instrument 180 directed through the sealing member 282.

A plurality of the sealing members 282 can be simultaneously used, as indicated in FIG. 19. Each sealing member has an annular skirt 298 that serves a spacing function to be certain that there is sufficient space so that the flaps 288 can move to their open position without interference from an adjacent sealing member 282.

In FIG. 11, a modified form of end fitting, according to the present invention, is shown at 300. The end fitting 300 has a body 302 with a reduced diameter neck 303 which is threadably connected to the sleeve 12 proximal to the sealing means 318 to be readily assembled to and disassembled from the sleeve 12.

A body 302 has an upwardly opening, cup-shaped configuration so as to define a receptacle 304 for a sealing member 306.

The sealing member 306 is in the form of a strip having an integrally formed, continuous outwardly projecting male element 308 and inwardly opening female receptacle 310. The male element 308 cooperates with the female receptacle 310 to allow the sealing member 306 to be spirally wrapped upon itself and maintained in this spiraled state. Depending upon how tightly the sealing member 306 is wrapped upon itself, the effective diameter of the inside surface 312 of the smallest turn 314, and thus that of the entire sealing member 306, can be selected. A loosely wound sealing member 306 produces a large diameter and a tightly wound sealing member 306 produces a smaller diameter.

If desired, an optional sealing cap 316 can be placed over the smallest turn 314 to thereby fix the configuration of the sealing member 306. The cap 316 can further be constructed to afford a redundant seal around the instrument 180 directed through the wrapped sealing member 306. A number of different size caps 316 can be used depending upon how the sealing member 306 is configured.

A second, optional sealing means, shown schematically at 318, can be provided on one of the sleeve 12 and end fitting 300 to completely block the sleeve passageway 320. The sealing means 318 can be selectively closed and opened and may be, for example, a mechanism such as any of those shown in FIGS. 3–7 in this application.

With the structure in FIG. 11, the sealing means 3 18 can be closed at the start of a procedure. The sealing member 318 can then be placed in the body 302 and wrapped to the desired configuration after which an appropriate end cap 316 placed on the outer turn 314. The instrument 180 can be directed through the cap 316 and wrapped sealing member 318 until it encounters the sealing means 318, which can then be placed in the open position to allow the instrument 180 to proceed therebeyond and into the cavity 20. The sealing means 318 effectively prevents escape of gas through the passageway 320 before the instrument 180 is sealingly engaged by the cap 316.

To remove the instrument 180, the instrument 180 is drawn upwardly beyond the sealing means 318 and the sealing means 318 is then closed before the instrument 180 is withdrawn fully from the end firing 300. This avoids inadvertent escape of gas as the instrument 180 is withdrawn, as to allow another instrument 180 to be substituted.

In FIG. 11A, an end firing, slightly modified from that in FIG. 11, is shown schematically at 326. The end firing 326 is not reduced in diameter at the base 328 thereof that threadably connects to the cannula sleeve 12. As a result, the end firing 326 will accommodate a significantly larger instrument 180 than the end firing 300. For example, the sealing member 306 can be configured to accommodate a 10 mm diameter instrument which is the largest instrument that the cannula sleeve 12 will accept. By reconfiguring the sealing member 306, any instrument size less than 10 mm can be accommodated. For example, the sealing member 306 can be reduced to accommodate a 5 mm diameter instrument, as shown in FIG. 11A, or any size therebetween. In this case, the smallest turn 314 stabilizes the instrument 180 which is only loosely received in the cannula sleeve 12.

The invention affords a substantial amount of versatility by allowing a single sleeve 12 to receive different end fittings capable of affording a positive seal while accommodating different types of instruments.

DESCRIPTION OF THE PREFERRED EMBODIMENT

Figure 25:
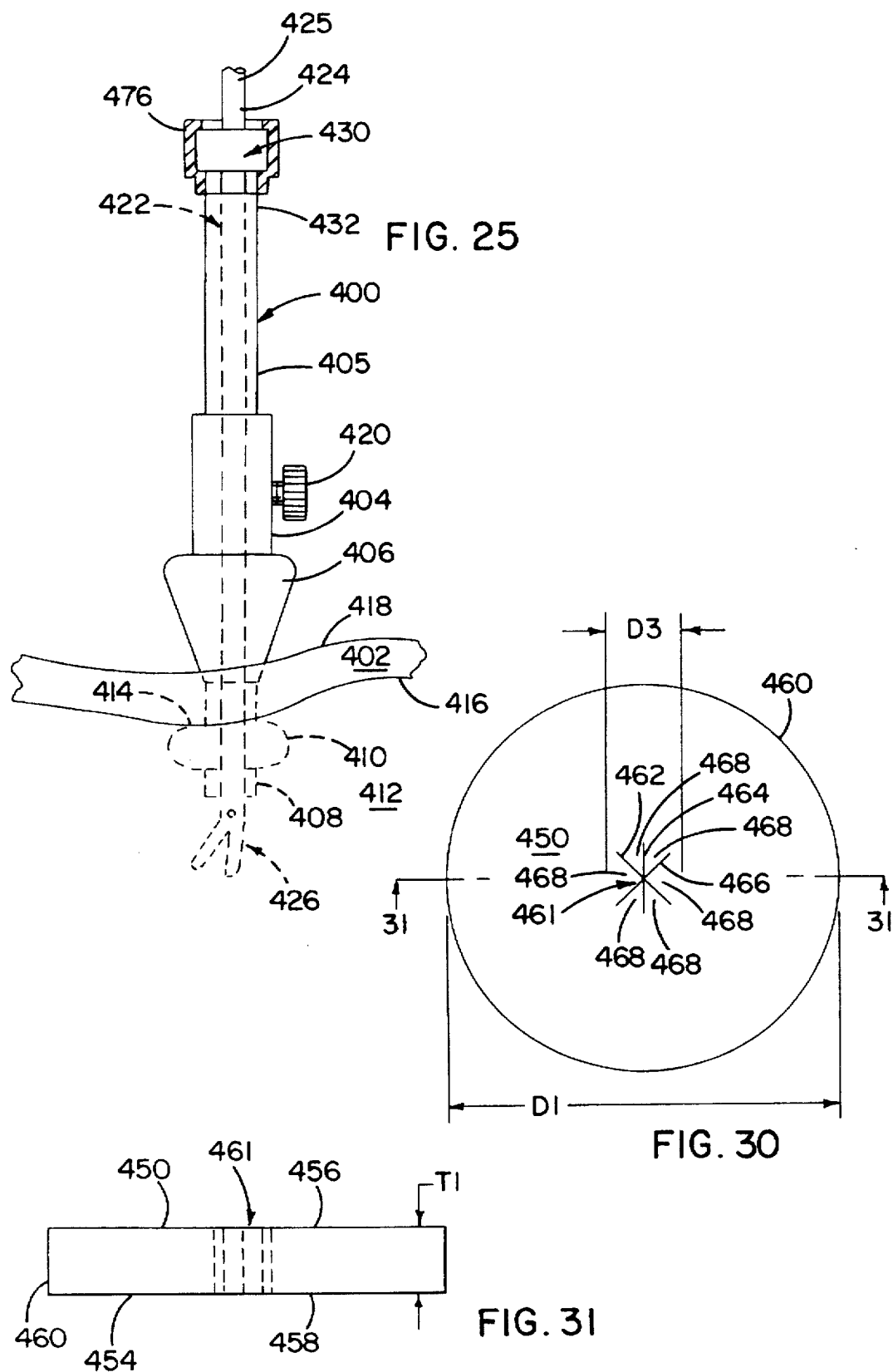
FIG. 25 is a side elevation view of a laparoscopic cannula captively held on a tissue, with an elongate medical instrument extended through the cannula and into a body cavity bounded by the tissue, with there being a preferred form of sealing structure, according to the present invention, on the proximal end of the cannula.

In FIG. 25, a laparoscopic cannula at 400 is shown captively embracing a tissue 402. The cannula 400 has a sleeve 404 which is slidable lengthwise of the body 405 of the cannula 404, and a conically-shaped nose 406 that can be sealingly pressed into the tissue 402. At the distal end 408 of the body 405, an inflatable membrane 410 is provided. The membrane 410, which is inflated after it is directed through the tissue and into an operating cavity 412, defines an annular shoulder 414 which is abuttable to the inside surface 416 of the tissue 402. To fix the cannula 400 on the tissue in an operative state, the cannula 400 is drawn upwardly to seat the shoulder 414, whereupon the sleeve 404 is pressed downwardly against the outside surface 418 of the tissue 402 to sealingly captively hold the tissue 402 between the membrane 410 and the sleeve 404. A set screw 420 can then be tightened against the body 405 to fix the relative positions of the sleeve 404 and membrane 410.

With this arrangement, a passageway 422 is defined by the cannula 400 through the tissue 402 into the operating cavity 412. In FIG. 25, an elongate medical instrument 424, with a generally cylindrical body 425, is shown directed through the passageway 422 so that a working head 426, at the distal end thereof, is situated within the cavity 412. The medical instrument 424 is only exemplary of the many different types of instruments that could be directed through the cannula 400.

As previously noted, it is necessary to direct a gas into the operating cavity 412 to distend the tissue 402 to create the necessary working space in the cavity 412. To confine the gas in the cavity 412 and passageway 422, in open communication therewith, sealing structure according to the present invention, as shown at 430, is provided at the open proximal end 432 of the cannula 400. As described in more detail below, the sealing structure 430 allows the instrument 424 to be withdrawn from the cannula 400 and another instrument to be substituted therefor without significant loss of gas from the cavity 412 and passageway 422. The details of the sealing structure 430 are shown in FIGS. 26-33.

Figure 28:
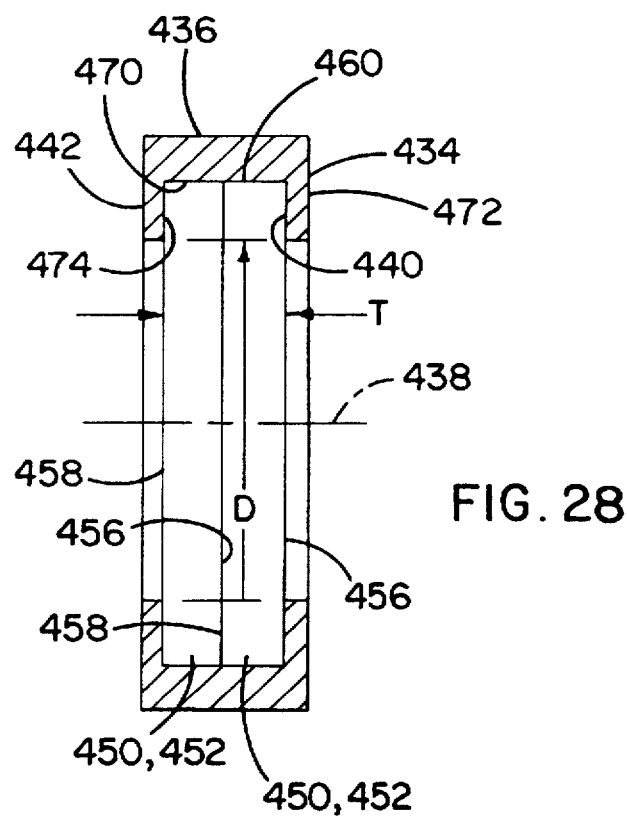
FIG. 28 is a view as in FIG. 27 with two sealing members in operative relationship with each other and in assembled relationship with the housing.
Figure 29:
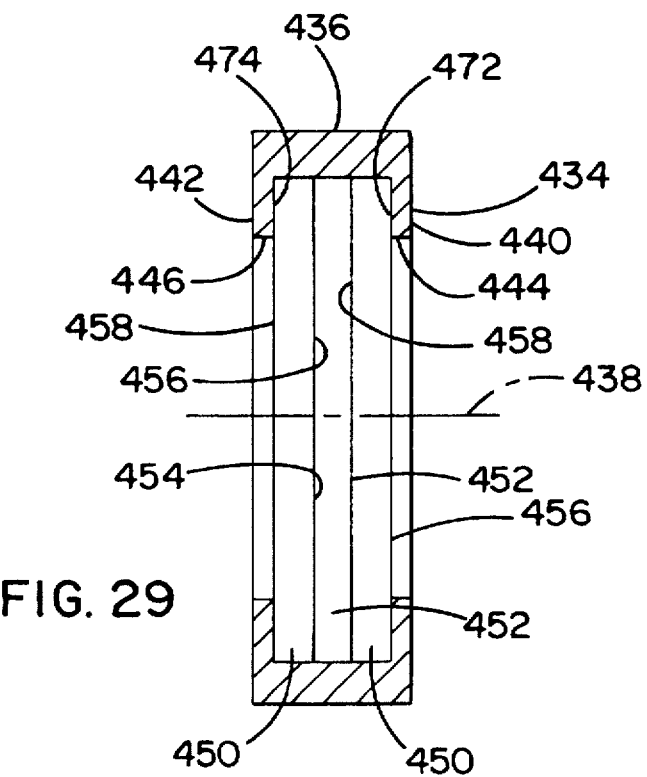
FIG. 29 is a view as in FIG. 28 with there being three sealing members.

More particularly, the sealing structure 430 consists of an annular housing 434 having a peripheral wall 436 extending around a central axis 438. Axially spaced, annular, first and second rims 440, 442 project radially inwardly from the wall 436 and have inner edges 444, 446, each having a diameter (D). The wall 436 and rims 440, 442 cooperatively define a receptacle 448 for two sealing members 450, 452 as shown in FIG. 28, or three sealing members 450, 452, as shown in FIG. 29. The housing 434 is preferably made from metal, such as stainless steel, or a hard plastic.

With the two sealing member arrangement in FIG. 28, each sealing member 450, 452 preferably has a construction as shown in FIGS. 30 and 31, although one could have the construction shown in FIGS. 32 and 33. The sealing member 450 has a body 454 made from a material that is compressible and deformable. In a preferred form, the body 454 is made from a silicone material having a durometer of 70.

The body 454 has a disc shape with oppositely facing flat surfaces 456, 458 and a peripheral edge 460. The edge 460 has a diameter (D1). An opening 461 is provided in the body 454 to allow passage therethrough of the instrument 424. In this case, three crossing slits 462, 464, 466 define the opening 461. The slits 462, 464, 466 define six triangular flaps 468 which readily deform relative to each other and the remainder of the body 454 upon introduction of the medical instrument 424. The slits 462, 464, 466 shown result in the opening 461 having an effective diameter (D3), as shown in FIG. 30.

In the arrangement shown in FIG. 28, the sealing members 450 in assembled relationship, are placed facially against each other, i.e. with the surfaces 456, 458 on the sealing members 450 against each other over the entire radial extent of the sealing members 450. The sealing members 450 are placed in operative relationship with the housing 434 by pressing the sealing members 450 into the receptacle 448. Since the edge diameter (D1) for the sealing members 450 is greater than the diameter (D) of the rim edges 444, 446, this is accomplished by radially compressing the sealing members 450 to direct them axially past either of the rims 440, 442. Once each deformed sealing member 450 situates fully within the receptacle 448, it assumes its undeformed state in which the outer edge 460 thereon nests snugly within the inside annular wall surface 470. With both members 450 in the receptacle, the combined thickness T of the members 450 substantially equal to the spacing between axial facing rim surfaces 472, 474. The sealing members 450 are thus snugly held within the housing 434 in such a manner as to define a self-contained subassembly that can be attached to the cannula end 432 by any suitable means known to those skilled in the art, as by a threaded cap 476, as shown in FIG. 25.

In FIG. 29, the housing 434 is constructed in a similar fashion although the spacing between the rim surfaces 472, 474 may be greater. Two of the sealing members 450 are employed as in FIG. 28, with an additional sealing member 452, as shown in detail in FIGS. 32 and 33 sandwiched therebetween. The sealing member 452 has a disc-shaped body 478 with oppositely facing, flat surfaces 480, 482, a peripheral edge 484, and an opening 486 through the thickness of the body 478. The body 478 is preferably made from the same material as the body 454 of the sealing members 450.

The principal difference between the sealing member 452 and the sealing member 450 is that the opening 486 in the former is defined by a cylindrical cutout as opposed to by one or more slits.

As the instrument 424 is directed from left to right through the sealing structure 430 as shown in FIG. 29, it initially contacts the flaps 468 defining the opening 461 through the body 454. The force of the advancing instrument 424 urges the flaps 468 axially and simultaneously effect a progressive radial depression thereof. The diameter (D4) of the opening 486 on the center sealing member 452 is chosen to be slightly less than the effective diameter (D3) of the opening 461 defined by the slits 462, 464, 466 in the sealing member 450. As a result, the body 478 of the center sealing member 452 provides axial support to the flaps 468 on the sealing member 450 as the instrument 424 is introduced. As a result, the instrument 424 effects a substantial radial compression of the flaps 468 between the instrument 424 and the housing wall 436. This results in a conforming of the sealing member 450 to the instrument body 425 and positive gripping force being applied by the body 454 around the instrument 424.

As the instrument 424 progresses through the opening 486, it effects a slight radial enlargement thereof. That is, preferably the opening 486 has a diameter (D4) that is slightly less than that of the instrument 424. As the instrument 424 progresses through the opening 486, it encounters the innermost sealing member 450 and effects slight axial deformation of the flaps 468 and radial compression thereof against the wall 436. As the instrument is backed out, the sealing member 450 on the right in FIG. 29 is axially reinforced against the sealing member 452 so that there is principally radial deformation of the flaps 468 thereon to create a positive seal around the instrument.

The separate sealing members 450, 452 provide redundant sealing. They also cooperate with each other to allow smooth guided movement of the instrument 424 through the sealing members 450, 452 while wiping foreign matter from the instrument 424 as it progresses.

The housing 434 also contributes radial and axial reinforcement to the sealing members 450, 452. As a result, the flaps 468 tend to more readily radially deform to conform around the outside of the medical instrument 424.

In one exemplary form of the invention, the individual sealing members 450, have a thickness (T1) that is no more than ¼ inch. More preferably, the thickness (T1) is on the order of 1/16 of an inch.

In one form, the diameter ODD of the peripheral edges 460, 484 is on the order of 0.8 inches. The effective opening diameter (D3) for the sealing member 450 is approximately 0.15 inches. The opening 486 in the sealing member 452 is approximately 0.1 inch. The housing wall 436 has an axial dimension (X) equal to approximately 0.25 inches. The thickness (X1) of each rim 440,442 in the axial direction is approximately 0.015 inches. The diameter X2 of the receptacle 448 is approximately 0.81 inches.

The foregoing disclosure of specific embodiments is intended to be illustrative of the broad concepts comprehended by the invention.

We claim:

1. A sealing structure for an elongate medical instrument, said sealing structure comprising:

a first sealing member having a first body with oppositely facing first and second surfaces and a peripheral edge;

a second sealing member having a second body with oppositely facing third and fourth surfaces and a peripheral edge; and a housing having a peripheral wall to surroundingly engage the peripheral edges of the first and second bodies with the first and second sealing members in operative relationship, said first body having at least a first portion that is compressible and deformable, said second body having at least a second portion that is compressible and deformable, there being an opening in the first portion of the first body that has a central axis extends through the first body from the first surface to the second surface, there being an opening in the second portion of the second body that has a central axis extends through the second body from the third surface to the fourth surface, the openings in the first and second bodies being expandable to allow the first and second bodies to grippingly engage an elongate medical instrument extended through the openings in the first and second bodies with the first and second sealing members in operative relationship the second surface on the first body facially abutting to the third surface on the second body with the first and second sealing members in operative relationship with the first and second sealing members substantially undeformed along the central axis of the openings in the first and second bodies.

2. The sealing structure according to claim 1 wherein the housing wall is rigid so that an elongate medical instrument extended through the openings in the first and second bodies with the first and second sealing members in operative relationship compresses the first and second portions of the bodies against the peripheral wall of the housing.

3. The sealing structure according to claim 1 wherein the first and second portions on the first and second bodies comprise silicone rubber.

4. The sealing structure according to claim 1 wherein the openings in the first and second portions of the first and second bodies have a different configuration.

5. The sealing structure according to claim 1 in combination with an elongate medical instrument having a substantially cylindrical body extending through the openings in the first and second portions of the first and second bodies.

6. The sealing structure according to claim 1 wherein the second and third surfaces are substantially flat.

7. The sealing structure according to claim 1 wherein the second and third surfaces are substantially flat over the entire extent of the second and third surfaces within the peripheral wall of the housing.

8. The sealing structure according to claim 1 wherein the first body has a thickness between the first and second surfaces that is no more than ¼ inch and the second body has a thickness between the third and fourth surfaces that is no more than ¼ inch.

9. The sealing structure according to claim 8 wherein the thicknesses between the first and second surfaces on the first body and third and fourth surfaces on the second body are each approximately 1/16 inch.

10. The sealing structure according to claim 1 wherein the housing has a center axis around which the peripheral wall extends and the housing has a first rim projecting radially inwardly from the peripheral wall and a second rim spaced axially from the first rim and projecting radially inwardly from the peripheral wall, the first and second sealing members residing closely captively between the first and second rims with substantially the entirety of the second and third surfaces facially abutting to each other with the first and second sealing members in operative relationship and in assembled relationship with the housing.

11. The sealing structure according to claim 10 wherein the peripheral edge of the first body has a first effective diameter, the first rim has a radially inwardly facing edge defining a second effective diameter and the first effective diameter is greater than the second effective diameter so that the first body must be radially compressed to be placed between the first and second rims on the housing.

12. The sealing structure according to claim 11 wherein the peripheral edge of the second body has a third effective diameter, the second rim has a radially inwardly facing edge defining a fourth effective diameter and the third effective diameter is greater than the fourth effective diameter so that the second body must be radially compressed to be placed between the first and second rims on the housing.

13. The sealing structure according to claim 1 including a third sealing member having a third body with oppositely facing fifth and sixth surfaces and a peripheral edge, with the first, second and third sealing members in operative relationship, the fifth surface on the third body facially engages the fourth surface on the second body, the third body having at least a third portion that is compressible and deformable, there being an opening in the third portion of the third body that extends through the third body from the fifth surface to the sixth surface, the opening in the third body being expandable to allow the third body to grippingly engage an elongate medical instrument extended through the opening in the third body, the peripheral wall of the housing surroundingly engaging the peripheral edge of the third body with the first, second and third sealing members in operative relationship with each other and in assembled relationship with the housing, the openings in the first, second and third portions of the first, second and third bodies being aligned with the first, second and third sealing members in operative relationship with each other and in assembled relationship with the housing to allow an elongate medical instrument to be directed guidingly through the first, second and third openings, to thereby be grippingly engaged by the first, second and third bodies.

14. The sealing structure according to claim 13 wherein the opening in the second portion of the second body comprises a substantial cylindrical cutout.

15. The sealing structure according to claim 14 wherein the opening in at least one of the first and third portions of the first and third bodies comprises at least one slit.

16. The sealing structure according to claim 15 wherein the opening in the at least one of the first and third portions of the first and third bodies comprises crossing slits which define independently movable and deformable flaps.

17. The sealing structure according to claim 16 wherein the crossing slits define at least six independently movable and deformable flaps in the at least one of the first and third portions of the first and third bodies.

18. A sealing structure for an elongate medical instrument, said sealing structure comprising:

a first disc-shaped sealing member having a first body with oppositely facing first and second flat surfaces and a peripheral edge;

a second disc-shaped sealing member having a second body with oppositely facing third and fourth flat surfaces and a peripheral edge; and a third disc-shaped sealing member having a third body with oppositely facing fifth and sixth flat surfaces and a peripheral edge, said first, second and third sealing members in an operative relationship engaging each other, said first body having at least a first portion that is compressible and deformable with there being an opening through the first portion extending from the first flat surface to the second flat surface, said second body having at least a second portion that is compressible and deformable with there being an opening through the second portion extending from the third flat surface to the fourth flat surface, said third body having at least a third portion that is compressible and deformable with there being an opening through the third portion extending from the fifth flat surface to the sixth flat surface, the openings in the first, second and third portions of the first, second and third bodies being aligned with the first, second and third sealing members in operative relationship so that an elongate medical instrument can be directed through the openings in the first, second and third portions of the first, second, and third bodies to be gippingly engaged by the first, second and third portions of the first, second and third bodies, the second flat surface on the first body facially abutting the third flat surface on the second body and the fourth flat surface on the second body facially abutting the fifth flat surface on the third body with the first, second, and third sealing members in the operative relationship, with the first, second and third sealing members substantially undeformed along the central axes of the openings in the first, second and third sealing members.

19. The sealing structure according to claim 18 in combination with an elongate medical instrument extended through each of the openings in the first, second and third portions of the first, second and third bodies.

20. The sealing structure according to claim 18 wherein the opening in each of the first and third portions of the first and third bodies being defined by at least one slit, the opening in the second portion of the second body being defined by a cutout.

21. The sealing structure according to claim 20 wherein the opening in each of the first and third portions of the first and third bodies is defined by a plurality of slits defining at least four independently movable and deformable flaps and the cutout in the second portion of the second body is substantially cylindrical.

22. The sealing structure according to claim 18 including a housing having a central axis and a peripheral wall extending around the central axis, a first rim extending radially inwardly from the peripheral wall and a second rim extending radially inwardly from the peripheral wall and spaced axially from the first rim relative to the central axis of the housing, the first, second and third sealing members in the operative relationship residing closely captively between the first and second rims and confined against movement axially relative to the housing by the first and second rims with substantially the entirety of the second and third flat surfaces facially abutting to each other and substantially the entirety of the fourth and fifth surfaces facially abutting to each other with the first, second and third sealing members in assembled relationship with the housing.

23. The sealing structure according to claim 22 wherein the opening in at least one of the first, second and third bodies is defined by at least one slit such that the opening in the at least one of the first, second and third body is substantially sealed in the absence of an elongate medical instrument being extended therethrough.

24. The sealing structure according to claim 23 wherein the opening in another of the first, second and third bodies is defined by a substantially cylindrical cutout in the another of the first, second and third bodies.

25. The sealing structure according to claim 24 wherein the first, second and third bodies comprise silicone rubber.

26. The sealing structure according to claim 25 wherein the first, second and third bodies each have a thickness between the oppositely facing flat surfaces thereon and the thicknesses of each of the first, second and third bodies is less than ¼ inch.

27. The sealing structure according to claim 26 wherein the first, second and third bodies each have a thickness between the oppositely facing flat surfaces, thereon and the thicknesses of each of the first, second and third bodies is approximately 1/16 inch.

* * * * *